(12) United States Patent
Delk et al.

(10) Patent No.: US 6,685,667 B1
(45) Date of Patent: Feb. 3, 2004

(54) ELECTRICALLY POWERED SURGICAL IRRIGATOR

(75) Inventors: Michael Delk, North Kingstown, RI (US); Augustus Felix, Cranston, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 239 days.

(21) Appl. No.: 09/668,178

(22) Filed: Sep. 22, 2000

Related U.S. Application Data (63) Continuation-in-part of application No. 09/481,120, filed on Jan. 11, 2000.

(51) Int. Cl.[7] .................................................. A61M 1/00
(52) U.S. Cl. ........................... 604/30; 604/151; 604/246
(58) Field of Search ...................... 604/30–33, 151–153, 604/27, 29, 246, 247, 248, 249, 254

(56) References Cited

U.S. PATENT DOCUMENTS

| | | | |
|---|---|---|---|
| 3,185,153 A | 5/1965 | Leucci | |
| 3,224,270 A | 12/1965 | Karol et al. | |
| 3,662,598 A | 5/1972 | Spencer | 73/194 E |
| 4,003,255 A | 1/1977 | Spencer | 73/194 E |
| 4,513,184 A | 4/1985 | Hughes | 200/81.9 |
| 4,604,089 A | 8/1986 | Santangelo et al. | 604/30 |
| 4,617,011 A | 10/1986 | Bloxom, Jr. | 604/27 |
| 4,669,453 A | 6/1987 | Atkinson et al. | |
| 5,142,271 A | 8/1992 | Bailey et al. | 340/606 |
| 5,222,946 A | 6/1993 | Kamen | 604/151 |
| 5,304,163 A * | 4/1994 | Bonnici et al. | 604/403 |
| 5,464,391 A | 11/1995 | DeVale | 604/67 |
| 5,484,402 A | 1/1996 | Saravia et al. | 604/35 |
| 5,807,313 A | 9/1998 | Delk et al. | 604/35 |
| 5,876,378 A | 3/1999 | Mbadugha | 604/152 |
| 6,099,494 A | 8/2000 | Henniges et al. | 604/35 |
| 6,106,494 A | 8/2000 | Saravia et al. | 604/35 |
| 6,162,194 A | 12/2000 | Shipp | 604/151 |
| 6,176,847 B1 | 1/2001 | Humphreys, Jr. et al. | |
| 6,261,266 B1 | 7/2001 | Jepson et al. | 604/201 |
| 6,436,072 B1 * | 8/2002 | Kullas et al. | 604/151 |

FOREIGN PATENT DOCUMENTS

WO 9523627 9/1995

* cited by examiner

*Primary Examiner*—Brian L. Casler
*Assistant Examiner*—Kevin C. Sirmons
(74) *Attorney, Agent, or Firm*—Darby & Darby (57) ABSTRACT

A surgical irrigator comprises a pumping unit connected to a handpiece by means of elongated irrigation tubing. The pumping unit includes an impeller, batteries and a battery powered motor to drive the impeller. The handpiece includes an irrigation valve which, when depressed, opens the valve and permits irrigation liquid to flow to the surgical site. A flow sensing device is positioned at the outlet of the pumping unit. When the irrigation valve is opened, liquid flow through the flow sensing device under the influence of gravity causes a float to move with the liquid. A light source provides a light beam which is interrupted by movement of the float. This is detected by a photosensor which generates a signal to turn the motor on, causing the pump to operate.

9 Claims, 8 Drawing Sheets

ELECTRICALLY POWERED SURGICAL IRRIGATOR

This is a continuation-in-part of U.S. patent application Ser. No. 09/481,120 filed Jan. 11, 2000 and entitled "Electrically Powered Surgical Irrigator".

This invention relates to surgical irrigators and, more particularly, to electrically powered surgical irrigators of the type used in endoscopic procedures.

BACKGROUND OF THE INVENTION

Today, numerous types of surgical irrigators are used for endoscopic surgery. One popular type of surgical irrigator, known as the Hydro-Surg Plus™ irrigator, is illustrated and described in Delk et al. U.S. Pat. No. 5,807,313 which is hereby incorporated by reference into this specification.

The surgical irrigator illustrated in the '313 patent is battery powered. It includes a small electrical motor which drives an impeller to force water under pressure from an irrigation bag to a handpiece enabling a surgeon to irrigate a surgical site through a wand or probe attached to the handpiece. In that particular case, the handpiece includes suction and irrigation lines which are controlled by trumpet valves. When the surgeon actuates the valve for the irrigation line, an electrical switch in the handpiece is closed which connects the motor to the batteries in the pumping unit, causing the pump to operate.

In the battery powered irrigators disclosed in the '313 patent and in Saravia et al. U.S. Pat. No. 5,484,402 the pump, battery and motor are retained in a housing which is spiked directly into the irrigation bag. The pump outlet is connected by tubing to the handpiece. Typically, the tubing is about ten feet long which means that the wire which connects the on/off switch in the handpiece to the batteries and motor in the housing is also ten feet long. Since there must be two wires, the total amount of additional wire required to position the switch in the handpiece is in the order of twenty feet. This length of copper wire results in a number of significant drawbacks as follows:

1. the wire itself is relatively expensive;
2. the weight of the copper wire adds to the weight of the tubing and, of course, the overall weight of the irrigator;
3. because the length of the wire is considerable, the added resistance diminishes the performance of the pump for a given battery source; and
4. the need to accommodate a switch in the handpiece detracts from the ergonomic design of the handpiece.

It is an object of this invention to provide an electrically powered surgical irrigator which avoids the above mentioned drawbacks of the prior art.

A more specific object of the invention is to provide a battery powered irrigator in which the switching mechanism for the pump motor is not connected to the motor by a substantial length of wire.

Furthermore, battery powered irrigators are not typically used in endoscopic procedures where body cavities are distended, i.e. arthroscopy and hysteroscopy. The reason is that it is necessary to maintain distension throughout the operation. This means that the pump must be on at all times and, very often, the battery life is not sufficient. It would be feasible, however, to use a battery powered irrigator for these procedures so long as the distension can be maintained when the pump is turned off from a lack of flow, for example if the outflow from the knee or the uterus is stopped.

Thus, it is a further object of the invention to provide a battery powered irrigator which can be used in endoscopic procedures such as arthroscopy and hysteroscopy, where body cavities are distended.

More particularly, it is an object of the invention to provide a battery powered irrigator in which the pump is actuated by liquid flow yet which is capable of maintaining pressure above atmospheric pressure when liquid flow is stopped.

Finally, in both of the above mentioned patents, the pumping unit includes a spike on its inlet port which is specially constructed so that when the pumping unit is attached to a conventional irrigation bag, the entire weight of the pumping unit is supported by the spike. Because the weight of the unit is considerable, the spike must include special support means such as a rib or it must be increased in diameter so as to create a friction fit which will support the unit. Regardless of which technique is used, the modified spike is relatively difficult to insert into a standard irrigation bag.

Accordingly, it is further object of the invention to provide a surgical irrigator in which a pump unit includes an inlet means with a spike which is easy to insert into a standard irrigation bag.

SUMMARY OF THE INVENTION

In accordance with a first feature of the invention, an electrically powered irrigation pump includes a pumping unit which is located in the vicinity of an irrigation bag and a handpiece connected by irrigation tubing to the pumping unit. A flow sensing device, connected at the output of the pumping unit, includes a float which moves when the surgeon opens the irrigation valve in the handpiece causing liquid to flow from the irrigation bag through the pumping unit. A photosensor detects movement of the float from its initial position. When it does so, it causes the circuit between the electrical source of power and the motor to close which then drives the impeller. When the irrigation valve in the handpiece is closed, the float returns to its initial position. This is detected by the photosensor which then causes the circuit between the power source and motor to open and the pump is turned off.

In the preferred embodiment, a one-way valve is placed in the input line between the irrigation bag and the pump. The one-way valve permits irrigant to flow into the pump but does not allow liquid to flow back into the irrigation bag when flow through the system stops, for example, by closure of the irrigation valve in the handpiece or by blockage of flow in an arthroscopic or hysteroscopic procedure. Thus cavity distension can be maintained in such procedures when flow is stopped.

In accordance with a further feature of the invention, the pumping unit includes clips which support the weight of the pumping unit on the IV pole or other device which holds the irrigation bag. The pumping unit includes a short flexible hose which is connected at one end to the inlet port of the pumping unit and at the other end to a conventional spike. The spike is coated with a lubricant such as silicone which makes it extremely easy for a nurse or other technician to attach the pumping unit to an irrigation bag.

DETAILED DESCRIPTION

Figures 1, 7:
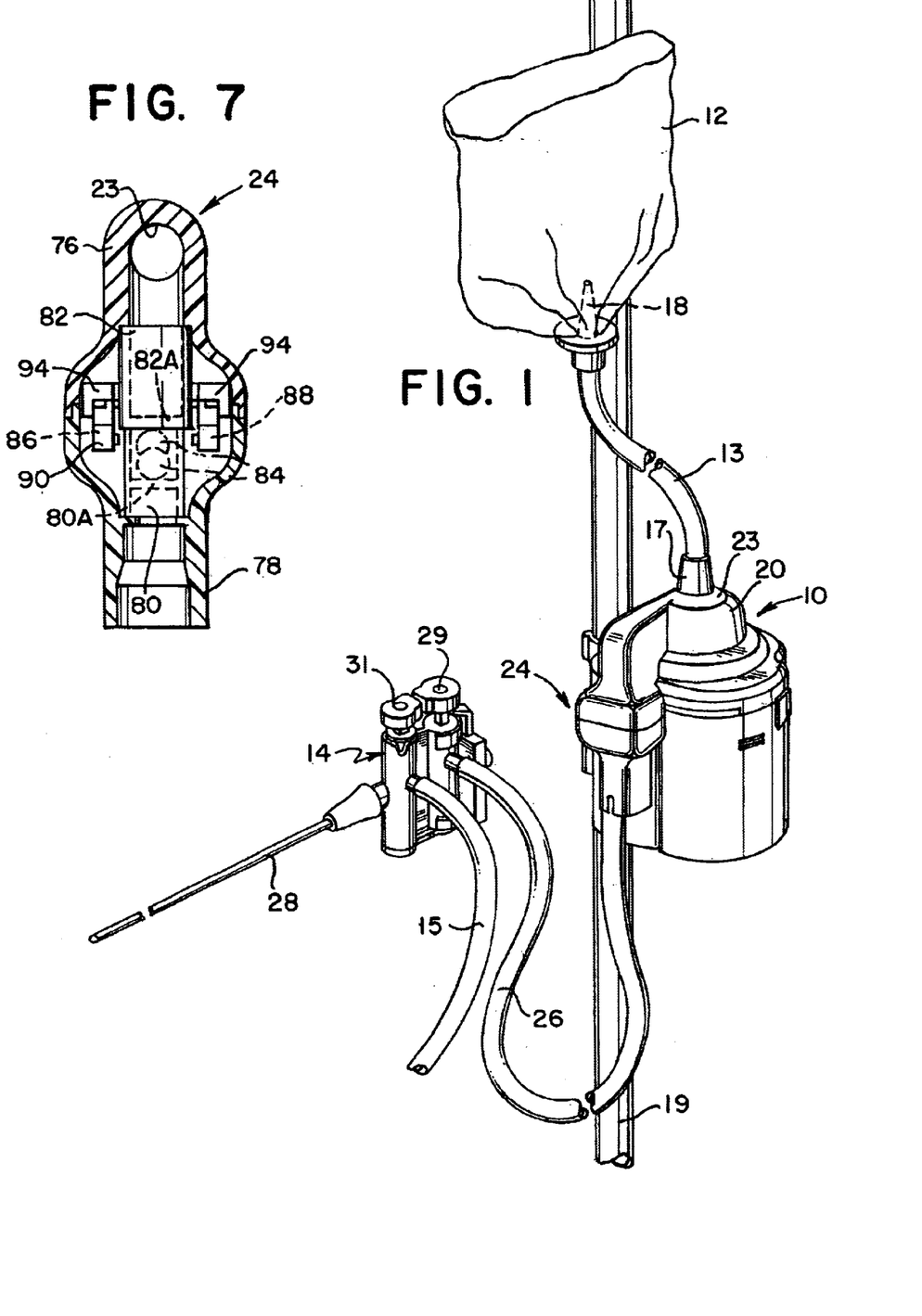
FIG. 1 is a perspective view of an irrigation system in accordance with a preferred embodiment of the invention.
FIG. 7 is a sectional view along the line 7—7 of FIG. 3.

FIG. 1 shows the main components of a surgical irrigator in accordance with the preferred embodiment of the invention. In this case, the device-illustrated provides irrigation and suction and is similar in construction to the irrigator/suction device shown in the '313 patent.

A battery powered pumping unit 10 is detachably secured at its inlet to an irrigation bag 12 (e.g. a saline bag) and, at its outlet, to a handpiece 14 which is also connected to a suction line 15. The pumping unit 10 receives irrigation liquid through an inlet port 17 which is attached to the bag 12 by means of a short flexible tube 13 and a spike 18. In accordance with one feature of the invention, spike 18 is a commercially available device and is coated with a lubricant such as silicone so that it can be easily spiked, i.e. inserted, into the conventional fitting of the irrigation bag. With this arrangement, the frictional force between the spike and bag is so low that it is unable to support the weight of the pumping unit 10. Accordingly, the pumping unit 10 also includes integrally formed clips 16 which are adapted to engage the IV pole 19 on which the irrigation bag 12 is supported. In use, a medical technician attaches the pumping unit to the IV pole 19 before the spike is inserted into the fitting of the irrigation bag 12. After the pumping unit and irrigation bag have been attached, the device is used in conventional fashion. The flexible tubing 13 is required to accommodate a situation in which the pumping unit 10 and bag 12 are not axially aligned, which is typical.

Pumping unit 10 includes a pump head 20 which includes the inlet port 17 and an outlet port 23 for directing irrigation liquid from the pump through a flow sensor 24 and flexible irrigation tubing 26 to the handpiece 14. Handpiece 14 directs irrigation liquid to an irrigation site within a patient's body through an elongate wand 28 that may be advanced to the irrigation site through a laparoscopic cannula. Trumpet valves 29 and 31 enable the surgeon to selectively couple the irrigation liquid or suction source, respectively, to the surgical site.

Figure 2:
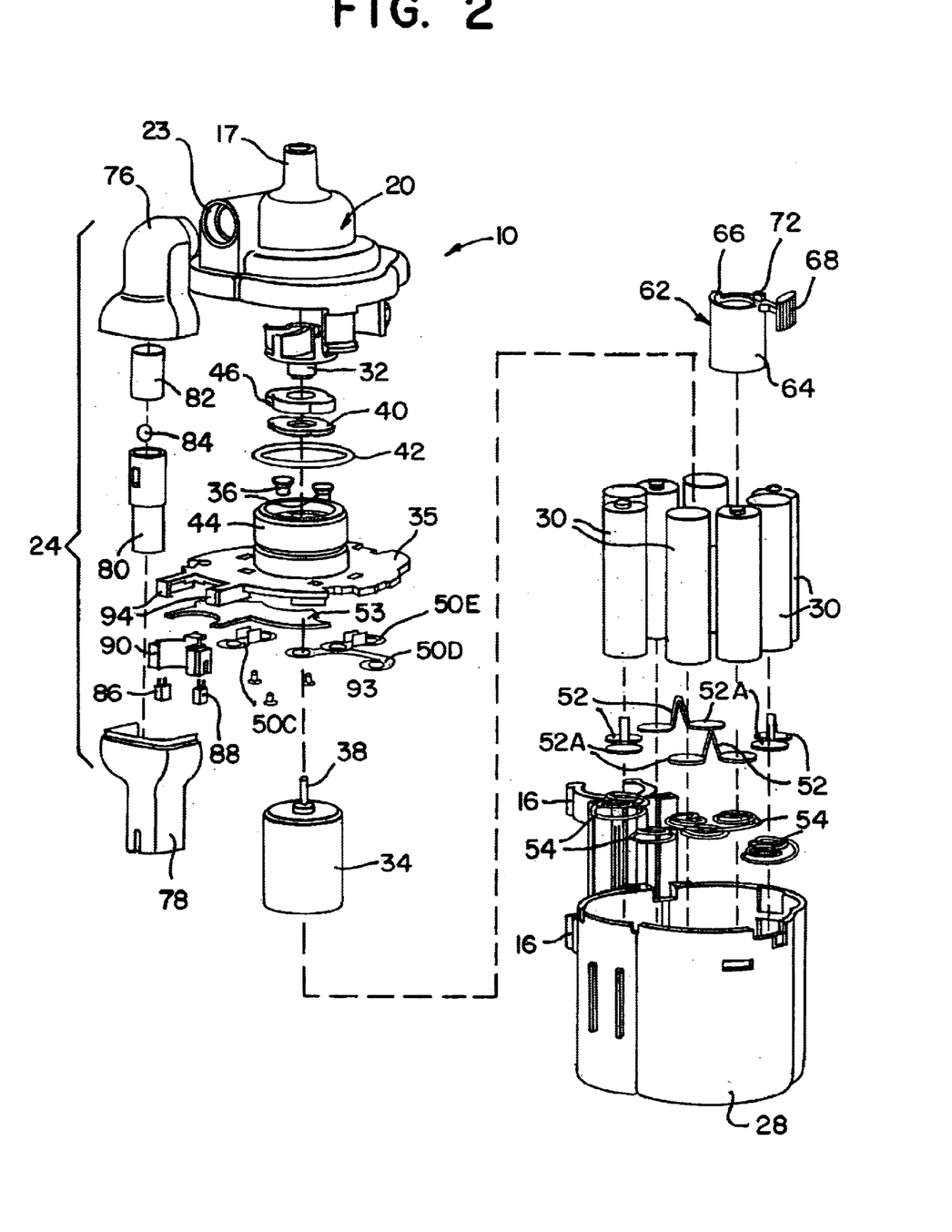
FIG. 2 is an exploded perspective view of a pumping unit in accordance with the preferred embodiment of the invention.
Figure 3:
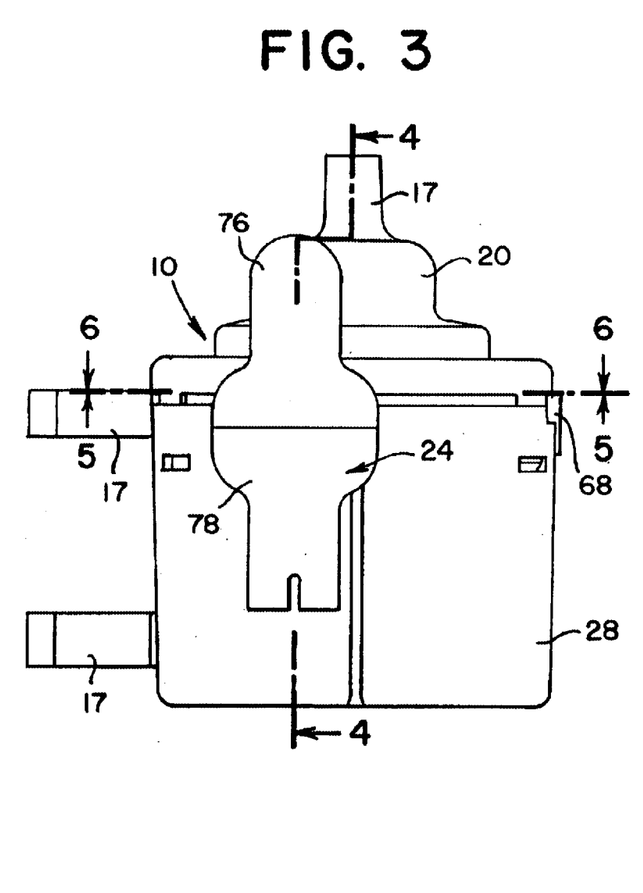
FIG. 3 is a side plan view of the pumping unit.
Figure 4:
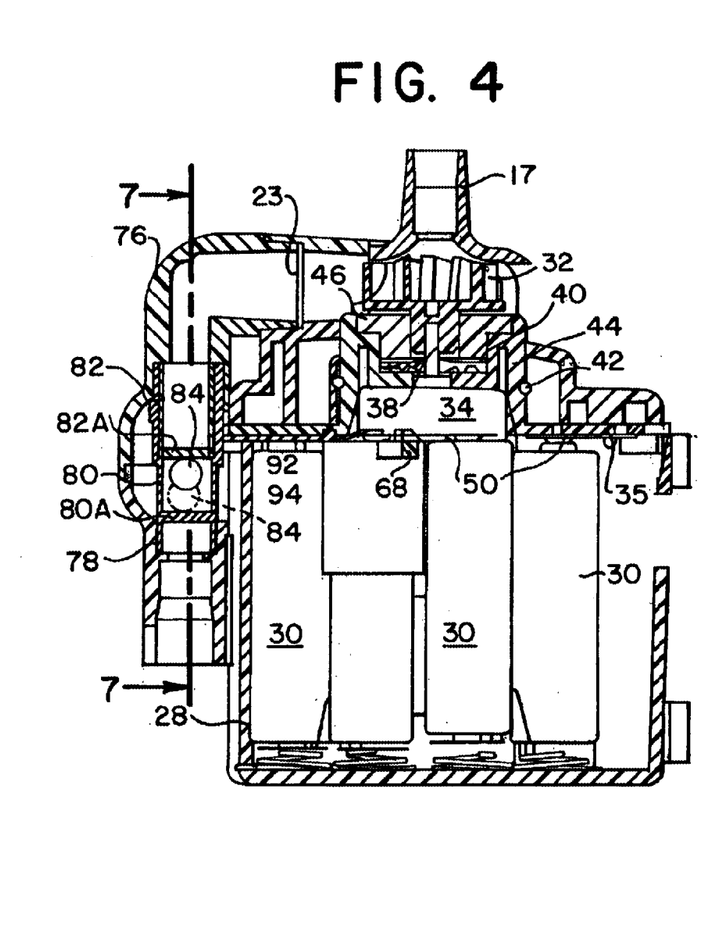
FIG. 4 is a side sectional view along the line 4—4 of FIG. 3.

The pumping unit 10 is similar to the pumping unit described in U.S. Pat. No. 5,807,313 and, accordingly, not all details are described herein. In addition to the pump head 20, it includes a battery case 28 which holds eight batteries 30 arrayed around the periphery of the case. The pumping unit further includes a deck 35 which rotatably supports an impeller 32 within the pump head 20. A motor 34 is attached to the bottom surface of deck 35 by means of screws 36 with its output shaft 38 extending through the deck and into the impeller 32. When the motor is connected to batteries 30, it will drive the impeller to pump irrigation liquid from the inlet port 17 to the outlet port 23.

The pumping chamber above deck 35 is sealed from the motor 34 and batteries 30 beneath the deck by a sealing gasket 40 and an O-ring 42 which is seated in a groove within an upstanding collar 44 on the deck 35. The gasket 40 is retained on the collar 44 by means of a seal retainer 46.

The batteries 30 are connected to motor 34 by five upper contacts 50A, B, C, D and E (FIG. 5) and four identical lower contacts 52. As explained in U.S. Pat. No. 5,807,313, the batteries 30 are connected in series with the motor 34. As shown in FIG. 2, each of the lower contacts 52 includes two flat discs 52A which are connected by a V-shaped connecting strip, with each of the discs contacting a lower terminal of one battery. Eight coil springs 54 at the bottom of the battery case apply pressure against the discs 52A of the bottom contacts 52 so that the lower contacts 52 and batteries 30 are spring biased against the upper contacts 50A, B, C, D and E. The upper contacts 50C, D and E connect positive and negative terminals of adjacent batteries together, but the contacts 50A and 50B are only connected to one battery terminal each. Contacts 50A and 50B are mounted on a printed circuit board (PCB) 53 which is described below. Contacts 50A and 50B are connected by circuit traces (not shown) on PCB 53 to the upper ends of two wires 56 which are soldered to terminals on the PCB. The other ends of the wires 56 are soldered to the motor terminals (not numbered). As shown best in FIG. 6, the batteries are held in place within battery case 28 by means of a series of projections 58 and 60 which extend upwardly from the floor of the case. The projections 58 each contact two adjacent batteries while the projections 60 are in contact with only a single battery.

Figure 8:
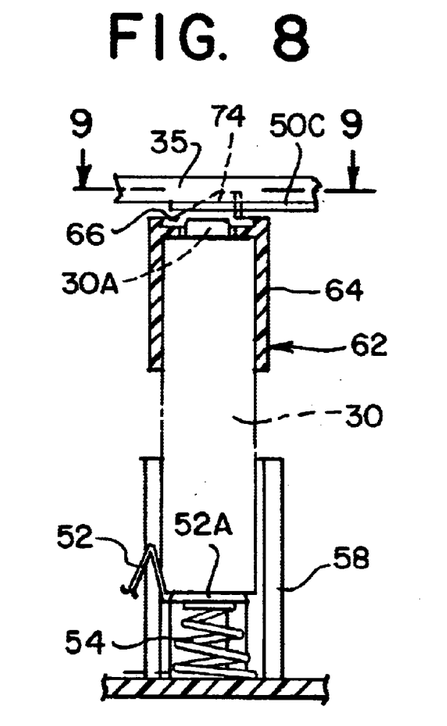
FIG. 8 is a side sectional view of the battery isolator switch.
Figure 9:
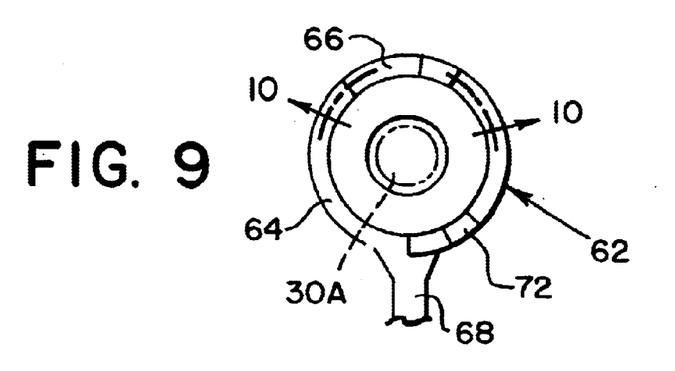
FIG. 9 is a top sectional view along the line 9—9 of FIG. 8.

In the preferred embodiment of the invention, a battery isolator switch 62 is provided to open the circuit between the batteries and motor prior to use, i.e. during transit and storage. (FIGS. 2 and 8–10) The battery isolator switch 62 includes a collar 64, which frictionally retains one of the batteries 30, and a cam 66 on the upper surface of collar 64. As best shown in FIG. 8, the collar 64 includes an upper plate 65 which has a central opening through which the positive terminal 30A of the retained battery 30 extends so that it can make electrical contact with the associated contact 50C when the isolator switch is "on". Cam 66 rides in a circular track (not numbered) within the undersurface of the deck 35. The collar 64 and its retained battery 30 are rotatable by turning a radially extending actuator arm 68 (see FIG. 6). An upward projection 72 diametrically opposed to the cam 66 stabilizes collar 64 during rotation.

Figure 10:
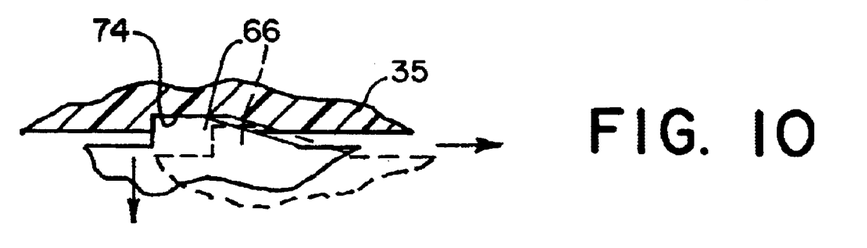
FIG. 10 is a sectional view along the line 10—10 of FIG. 9.

The groove within the undersurface of deck 35 includes a cam follower depression 74. When the switch is "off," i.e.

during transit and storage prior to use, with the collar 64 rotated to the "off" position, the cam 66 does not sit within the groove 74 and the terminal 30A of the battery 30 retained by collar 64 is pushed out of engagement with the upper contact 50C (FIG. 10). When the actuator arm 68 is rotated, cam 66 moves into the depression 74 and the coil spring 54 pushes the battery 30 into electrical contact with contact 50C. The motor can then be started as described below by the flow sensor when the irrigation valve is opened. To turn the system "off," the actuator arm 68 is rotated to lift the cam 66 from depression 74, pushing the battery terminal 30A away from the contact 50C.

The flow sensor 24 (FIGS. 2 and 4–7) comprises a top shroud 76 and a bottom shroud 78 which include mating surfaces that can be sealed in conventional fashion. The top shroud 76 serves as an elbow and its upper end is sealed to outlet port 23 of the pump. The two shrouds 76 and 78 together serve as a housing for the actual detector which includes a bottom sleeve 80 and a top sleeve 82. The upper portion of sleeve 80 is enlarged so that it can receive the top sleeve 82. Each sleeve 80, 82 includes a flat so that the angular positions of the two sleeves is fixed relative to each other. Sleeve 80 includes a lower cross bar 80A and sleeve 82 includes a lower cross bar 82A so that when the sleeves are assembled, the cross bars 82A and 80A serve as upper and lower stops, respectively, for a float or ball 84. In FIG. 7, the ball 84 is shown in phantom in both its up and down positions. When the sleeves are assembled with the flats in engagement, the cross bars 80A and 82A are parallel to each other.

After the device has been primed, i.e. the irrigation tubing 26 is filled with irrigating liquid, if the irrigation valve 29 is not pressed, the ball 84 will float within the cage formed by the sleeves with its upper movement limited by the cross bar 82A. When the irrigation valve 29 is depressed, liquid flow starts under the influence of gravity which drives the ball 84 downwardly into engagement with the lower cross bar 80A. It is this movement of the ball which is detected and used to start the motor.

In the preferred embodiment, a photodetector comprising an infrared (IR) light emitting diode (LED) 86 and phototransistor 88 are retained within a cradle 90 which is mounted on the printed circuit board 53. The PCB is secured to the bottom of the deck 35 by screws 93 (FIG. 2). Deck 35 includes flanges 94 which support the printed circuit board 53 and the cradle 90. The printed circuit board 53 contains the circuitry for actuating the light source, sensing the movement of the ball, and closing the circuit to the motor 34 as explained below with reference to FIG. 11. Since the movement of the ball is sensed optically, the material of sleeve 80 must be transparent to the optical energy which, in the preferred embodiment, is infrared. The ball is opaque to the optical energy and, as shown in FIG. 7, when it floats, i.e., when it is in the 'up' position, it blocks the passage of light from IR LED 86 to the phototransistor 88. When the ball moves under the influence of gravity to the down position, the optical path between LED 86 and phototransistor 88 is open.

Figure 11:
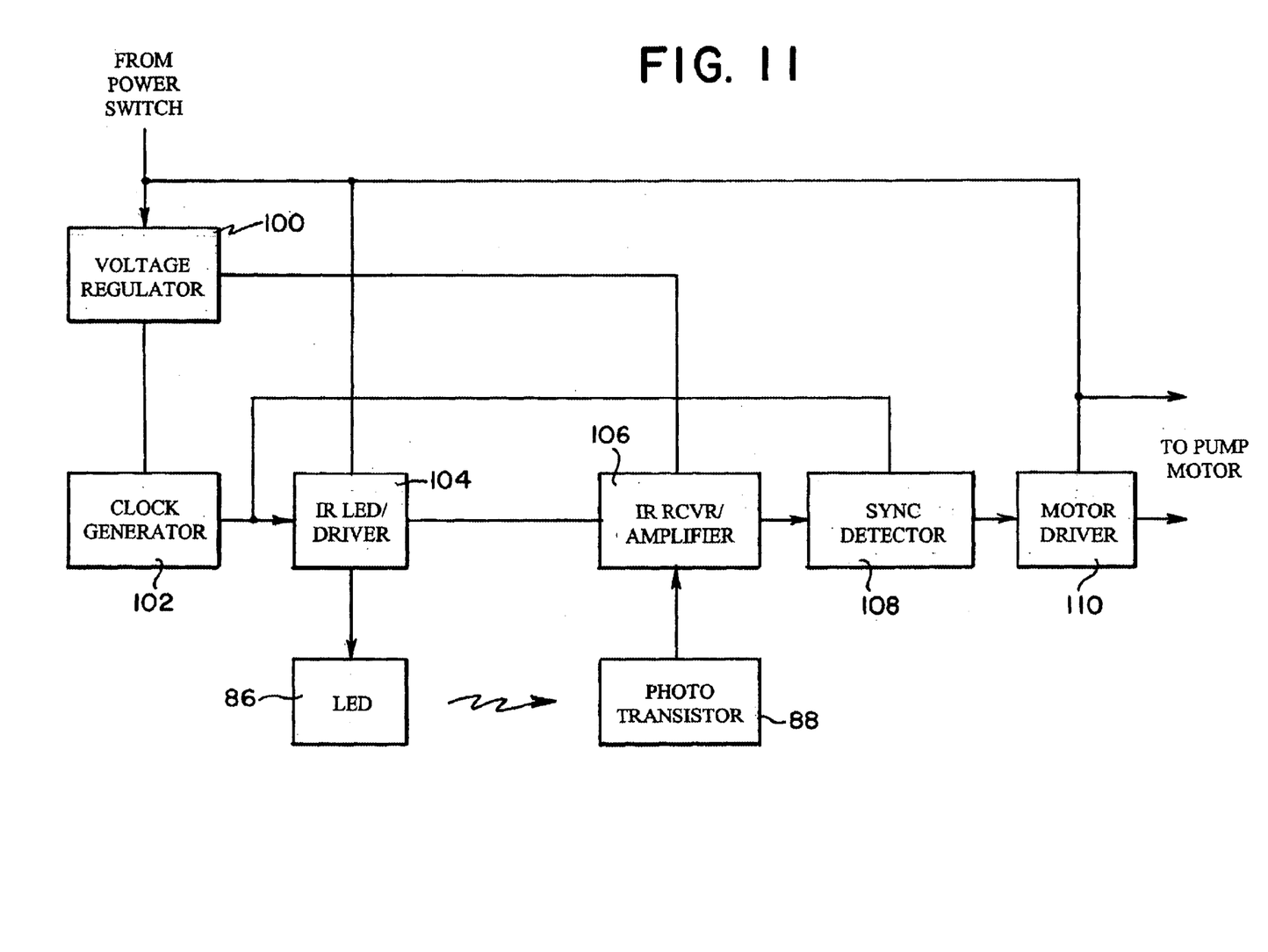
FIG. 11 is a block diagram showing the control circuitry of the flow sensor according to a preferred embodiment.
Figure 12:
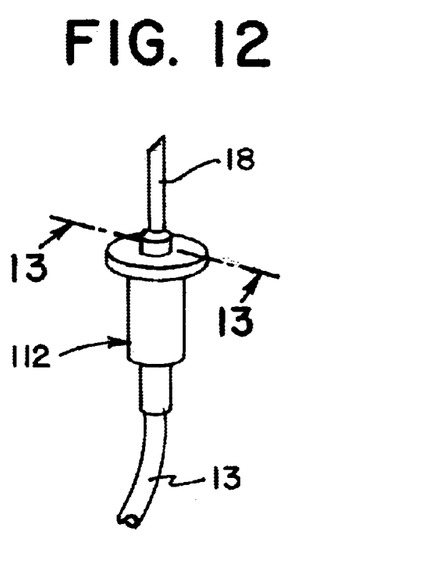
FIG. 12 shows a further embodiment of the invention in which a one way valve prevents irrigant from flowing into the irrigation bag when the irrigation valve is closed.

FIG. 11 illustrates in block diagram form one embodiment of the circuitry for driving the infrared LED 86, for sensing the down position of the ball 84, and for driving the motor 34. Voltages and frequencies referred to below are for purposes of explanation only. Obviously, many different optical sensing devices can be used to sense movement of the ball.

When the battery isolator switch 62 is turned on, twelve volts are applied to a voltage regulator 100 which produces a regulated voltage of 5.1 volts, for example. The voltage output from voltage regulator 100 is connected to a clock generator 102 which produces on its output a 4.5 Khz square wave. The output of the clock generator 102 is fed to an IR LED driver 104 which produces the pulses which drive the infrared LED 86. Driver 104 is powered by the 12 volt battery supply.

If the ball is in the up position, the optical path between the IR LED 86 and photosensor 88 is blocked and there is no signal. If, however, the ball is in the down position, the IR sensor 88 receives a pulsed optical signal from LED 86 which is coupled to an IR receiver/amplifier 106. Amplifier 106 is also powered by the 5.1 volt output from regulator 100. The output from amplifier 106 and clock generator 102 are fed to a synchronous integrating detector 108 which compares the data signal from the phototransistor 88 with the clock signal and produces an output when they are similar for a predetermined time duration. A static data signal will not cause a data output from detector 108 but a valid output will be generated even if random noise appears on the signal from the phototransistor 88. The detector 108 compares alternating phases of the clock signal and the data signal and produces an output only (a) when both signals are high, and (b) when both signals are low. The detector also introduces a time delay so that the motor is turned on a predetermined time after the irrigation valve 29 is opened (e.g. 10 ms), and the motor is turned off a predetermined time after the valve is closed (e.g. 15 ms). The detector output is coupled to a pump motor driver which starts (or stops) the motor.

The operation of the system is as follows. After the pumping unit 10 has been secured to the IV pole and the spike 18 inserted into the irrigation bag 12, the tubing 26 to the handpiece is mostly filled with air. The flow sensor ball 84 is in the down position and the battery isolating switch 62 is off.

To prime the system, the irrigation valve 29 is pressed, opening the valve and permitting irrigation liquid to flow from the irrigation bag 12 through tubing 26 and handpiece 14 by gravity. When the fluid path is filled with liquid, the irrigation valve 29 is released closing the valve. The sensor ball 84 then floats to the up position and the battery isolator switch 62 can be turned on. The motor 34 will remain off because the ball 84 is in the up position. The system is primed and ready for operation. When the irrigation valve 29 is depressed, liquid flows causing the ball 84 to move to the down position to turn on the motor as described.

The system can also be primed by using the pump. To do this, the irrigation valve 29 is opened and the switch 62 turned on. Because the ball is in the down position, the motor 34 will turn on and fill the fluid path. When the fluid path is filled with liquid, closing the irrigation valve will cause the flow sensor ball 84 to float to the up position.

In the embodiment shown in FIGS. 1–11, irrigant can flow from the pump through the spike 18 into the irrigation bag 12 when the irrigation valve 29 is closed. This can lead to a slight delay between the time the irrigation valve 29 is depressed and the time the powered irrigant stream reaches the surgical site. FIGS. 12–15 illustrate a valve construction which can be employed in a preferred embodiment of the invention to maintain pressure within the pumping system above atmospheric pressure when the irrigation valve 29 is closed or when the flow of irrigant is stopped for any reason.

As shown in FIGS. 12–15, a one-way valve 112 is placed in inlet line 13 immediately beneath the spike 18. As explained below, valve 112 allows liquid to flow from irrigation bag 12 to pumping unit 10 when the pump is on but does not permit backflow of the irrigant when the pump is turned off. Thus, when irrigation valve 29 is released (i.e. the valve is closed), the liquid within the pump system (between one-way valve 112 and irrigation valve 29) is maintained at a pressure above the pressure in the irrigation system caused by the liquid head. Thus, when irrigation valve 29 is depressed, the release of the stored energy moves the float 84 rapidly causing the pump to start operation almost immediately.

Another benefit of the one-way valve 112 is to prevent air bubbles within the system from affecting operation. Without the valve, as the pressure in the system tends to equilibrate when the irrigation valve 29 is released, air bubbles within the system will float upwardly toward the irrigation bag. As these bubbles pass the IR sensor 86, 88 (FIG. 7), they can unintentionally activate the motor. This is undesirable for a number of reasons. First, the surgeon expects the motor to turn off when the irrigation valve is not depressed. Secondly, the needless operation of the pump causes noise and can lead to overheating of the motor and unnecessary depletion of battery life. With one-way valve 112 in the inlet line 13, when irrigation valve 29 is released, any air bubbles in the system are locked within the pressurized system; therefore, they are not subject to movement which would cause the motor to turn on.

Figure 13:
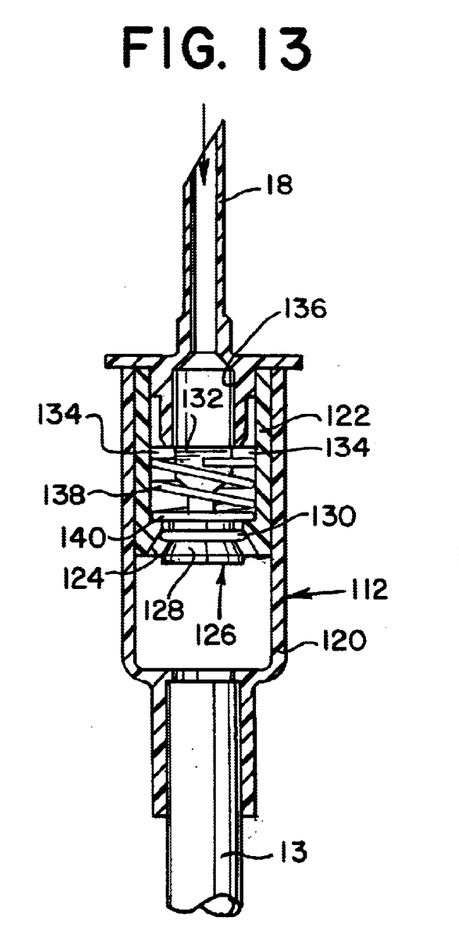
FIG. 13 is a side sectional view along the line 13—13 of FIG. 12 showing a preferred embodiment of a one-way valve in the closed position.
Figure 14:
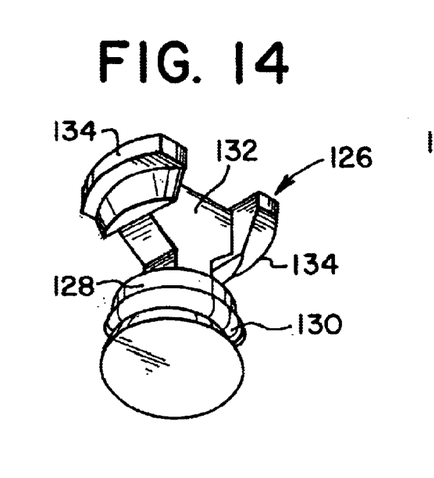
FIG. 14 is a perspective view of the valve body in accordance with a preferred embodiment.
Figure 15:
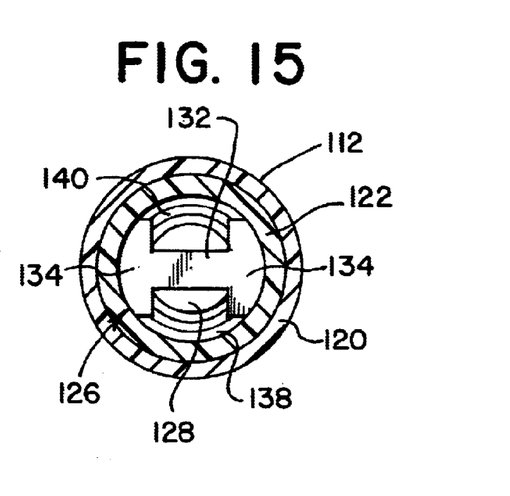
FIG. 15 is a sectional view along the line 15—15 of FIG. 13A.

The construction of a preferred one-way valve 121 is shown in FIGS. 13–15. The valve includes an exterior cylindrical housing 120 which is attached to the spike 18 at its upper end and to the inlet tube 13 at its lower end. A cylindrical internal seat 122 is fixed in the upper portion of housing 120 and includes a conical surface 124 which flares outwardly at its bottom and serves as a seat for a valve body 126.

Valve body 126, as shown in FIG. 14, includes a generally cylindrical base 128 which is flared at its lower end so that a sealing O-ring 130 can be held on the base. A cross piece 132 extends upwardly from base 128 and includes two outwardly extending retaining lips 134. As shown in FIG. 15, the width of the cross piece 132 is less than the diameter of the spike conduit 136. A coil spring 138 is compressed between the under surfaces of the retaining lips 134 and the upper surface of an internal rim 140 from which the conical seating surface 124 extends. Spring 138 urges the valve body 126 toward the spike 18 which biases O-ring 130 against the seating surface 124 to close the valve.

Figure 13A:
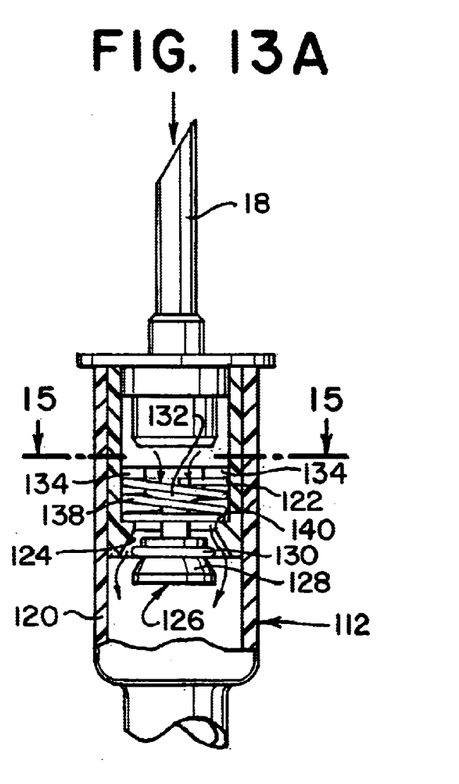
FIG. 13A is a side view partially in section showing the one-way valve in its open position.

When the irrigation valve 29 is closed, the valve body 126 is in the position shown in FIG. 13, i.e. valve 112 is closed. When the surgeon depresses valve 29, water starts to flow through spike 18 and conduit 136 due to gravity. The force applied by the water against the valve body 126 is greater than the retaining force applied by spring 138, causing the valve body to move downwardly to the position shown in FIG. 13A in which the irrigant flows past the O-ring 130 to the inlet tube 13. When irrigation valve 29 is released (i.e. closed), spring 138 returns the valve body to the position shown in FIG. 13 which closes the valve and prevents liquid from flowing upwardly through spike 18 into irrigation bag 12. This places the liquid in the pumping system under pressure. As a result, the motor is turned on almost immediately after valve 29 is depressed and the presence of air bubbles does not affect system operation.

Moreover, the pump can be used for endoscopic procedures where body cavities are distended (e.g. arthroscopy and hysteroscopy) because backflow of irrigant is prevented by the one-way valve when outflow from the cavity is stopped. This keeps the pressure in the system above the pressure due to the liquid head to maintain distension.

Numerous modifications of the invention are possible. Instead of IR energy, other optical frequencies can be used. In the embodiment shown in FIGS. 1–20, the optical beam is blocked when the ball is floating and unblocked when flow starts. As described below, the device may work in the opposite fashion, i.e. by blocking the optical path when flow starts (i.e. the ball is down). The basic principles of the invention do not depend on the type of photo detection employed.

Figures 16, 17:
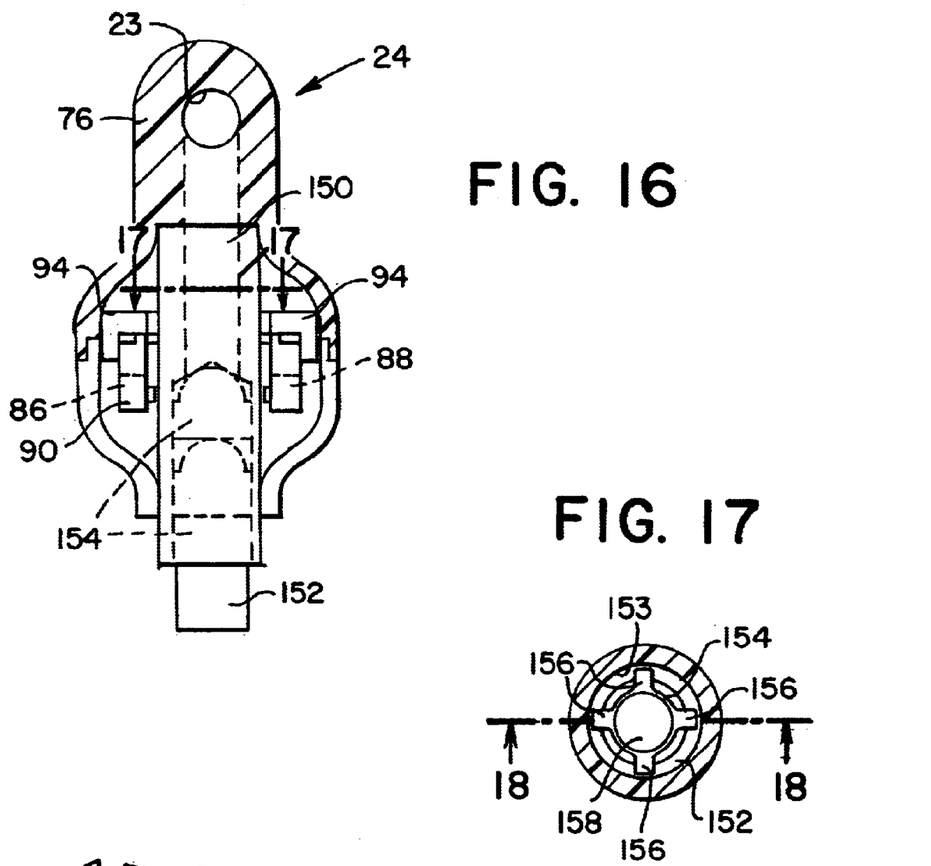
FIG. 16 is a front view partially in section of a flow-sensing device in accordance with a second embodiment of the invention.
FIG. 17 is a top sectional view along the line 17—17 of FIG. 16.
Figure 18:
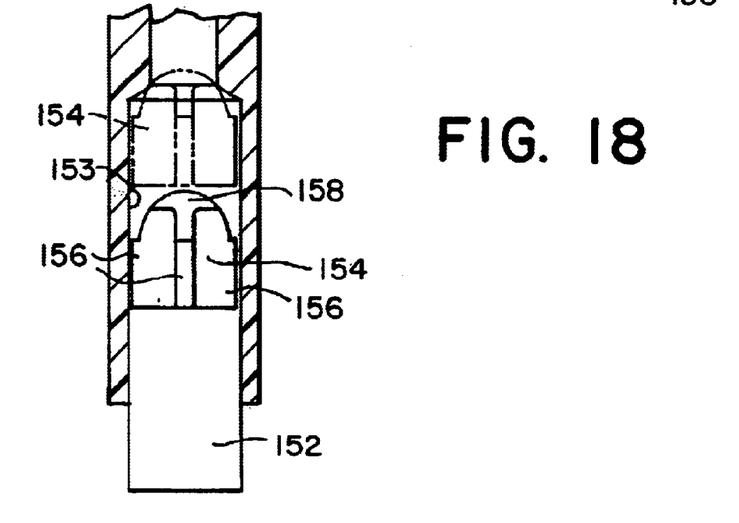
FIG. 18 is a front sectional view along the line 18—18 of FIG. 17.

FIGS. 16–18 illustrate a flow-sensing device in accordance with a second embodiment of the invention. Referring to those drawings, the bottom and top sleeves 80 and 82 of the first embodiment (FIG. 7) are replaced by a tubular member 150 and a lower sleeve 152 which retains the pump outlet tube 26. Tubular member 150 includes an enlarged diameter section or chamber 152 in which an opaque float/shutter 154 can move in response to liquid flow. The shutter 154 includes four fins 156 and an upper dome 158. The upper dome occludes the flow channel through tubular member 150 when the shutter is in its uppermost position as shown in phantom lines. The finned construction permits liquid flow when the shutter is driven to its lowermost position in which it abuts the upper end of sleeve 152.

Figure 5:
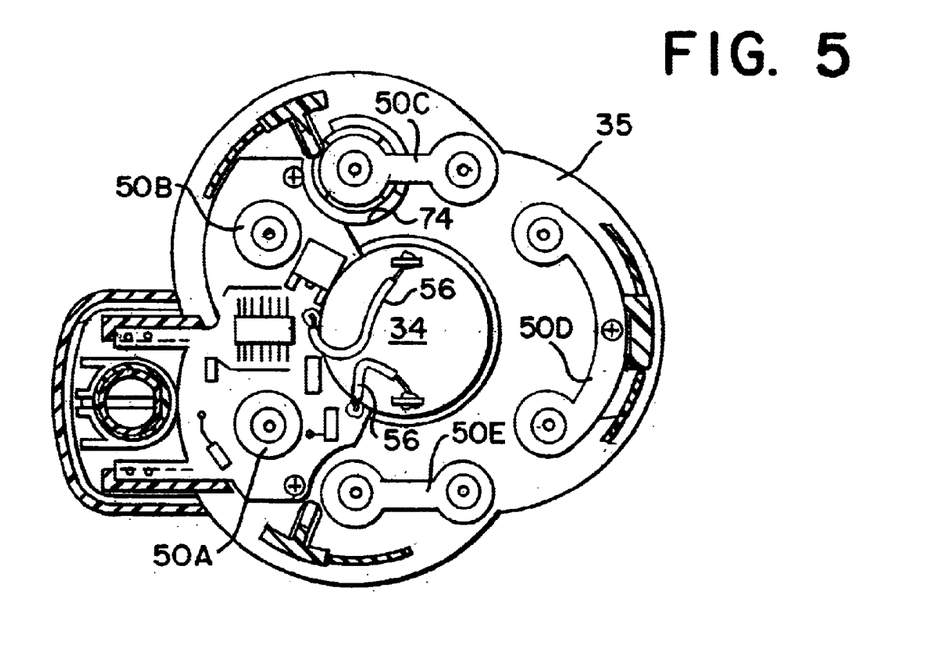
FIG. 5 is a top plan view along the line 5—5 of FIG. 3.
Figure 6:
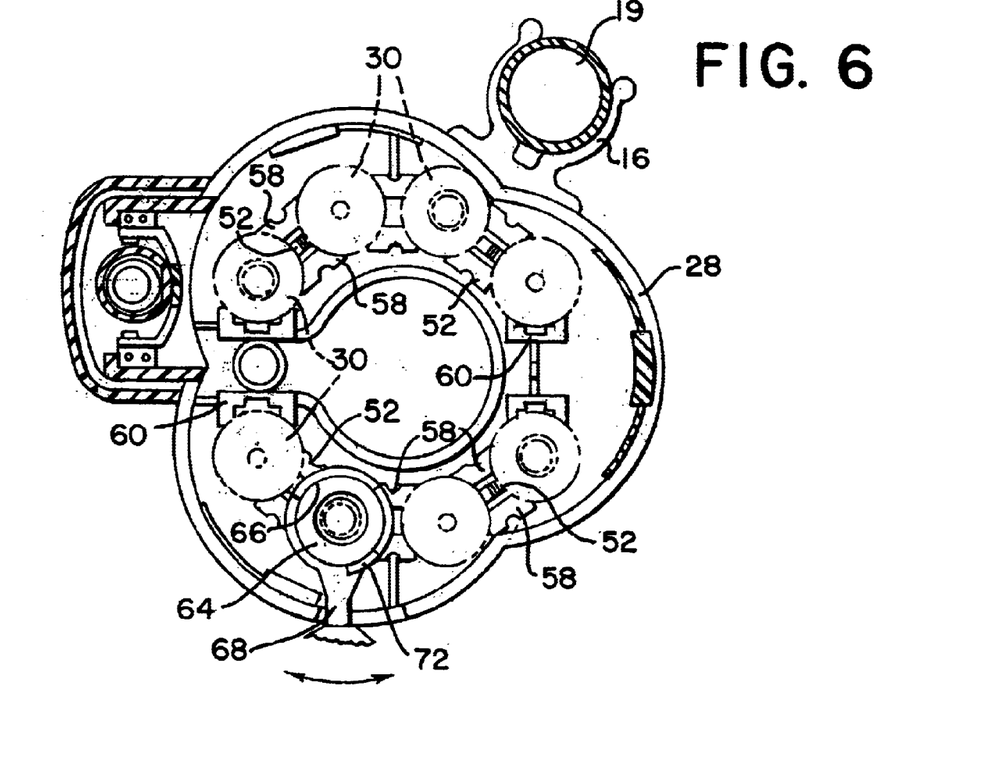
FIG. 6 is a top plan view along the lines 6—6 of FIG. 3.

Tubular member 150 may be made of polycarbonate or any other material transparent to optical energy which, in this embodiment, is also infrared. The infrared transmitter and receiver may be the same as illustrated in FIGS. 5–7. In this embodiment, however, when shutter 154 floats in its uppermost position, i.e. when no liquid is flowing through tubular member 150, the infrared beam passes from the transmitter through the transparent member 150 to the infrared receiver. When handpiece valve 29 is depressed and flow starts, the shutter is pushed downwardly to the position shown in solid lines in FIG. 18 where it interrupts the infrared light beam. The interruption of the beam is sensed by the circuit in the printed circuit board (see FIGS. 2 and 5) which then closes the energizing circuit to the motor.

In the illustrated embodiment, a surgical irrigator is used in conjunction with a handpiece of the type customarily used for laparoscopic surgery. As indicated above, the invention is also useful in other types of endoscopic procedures such as arthroscopy and hysteroscopy. As used herein, the term "handpiece" is intended to encompass handpieces of the type use for laparoscopic surgery as well as cannulas of the type used in arthroscopic and hysteroscopic surgery. The term irrigation valve is intended to include any device which starts and stops liquid flow to a surgical site.

What is claimed is:

1. A surgical irrigator comprising in combination, a pumping unit having an outlet, a handpiece, and tubing connecting the outlet of said pumping unit to said handpiece, said handpiece including an irrigation valve, said pumping unit including an impeller, batteries, upper and lower contacts for engaging the terminals of said batteries, and a battery powered motor for driving the impeller, an optical flow sensor for sensing liquid flow through said tubing when said irrigation valve is open, means responsive to said optical sensor for turning said motor on to drive said impeller, a manually operable switch for selectively moving at least one of the batteries out of electrical contact with one of its associated contacts, said manually operable switch including a rotatable arm and camming means responsive to rotation of said arm for moving said one battery.

2. A surgical irrigator according to claim 1, wherein said means for turning said motor on includes a detector responsive to said photosensor for connecting said motor to said batteries when said manually operable switch connects said batteries in circuit with said motor.

3. A surgical irrigator according to claim 1, wherein said impeller, batteries and battery powered motor are located in a housing having a deck which separates the impeller from the batteries and motor, and a printed circuit board attached to the deck in the same compartment as the batteries and motor, said light source, photosensor and means for turning said motor on being attached to said printed circuit board.

4. A surgical irrigator according to claim 1, further including a one-way valve connected between said inlet and a source of irrigation fluid for preventing liquid flow toward said source of irrigation fluid when the irrigation valve is closed.

5. A surgical irrigator for use with a source of irrigation liquid, comprising in combination, a pumping unit having an inlet and an outlet, outlet tubing connected to the outlet of said pumping unit, and a handpiece having an irrigation valve for initiating liquid flow through the pumping unit, said pumping unit including an impeller and an electrically powered motor for driving the impeller, the improvement comprising a flow sensor having a movable float for sensing liquid flow through said pumping unit when said irrigation valve is open, means responsive to movement of said float for turning said motor on to drive said impeller, and a one-way valve, located between said source of irrigation liquid and flow sensor applying a positive pressure to said float when the pumping unit is not operating so that the movement of the float is accelerated by said positive pressure when said irrigation valve is opened.

6. A surgical irrigator according to claim 5, wherein said flow sensor includes a float having a first position when the irrigation valve is closed and a second position when the irrigation valve is open.

7. A surgical irrigator according to claim 6, wherein said flow sensor includes a light source and a photosensor responsive to light from said light source, said float blocking the light path between the light source and photosensor in one of said positions.

8. A surgical irrigator according to claim 7, wherein said means for turning said motor on includes a detector responsive to said photosensor for connecting said motor to a source of electrical energy.

9. A surgical irrigator according to claim 5, wherein said one-way valve is connected between said inlet and said source of irrigation liquid.

\* \* \* \* \*